Figure 1:
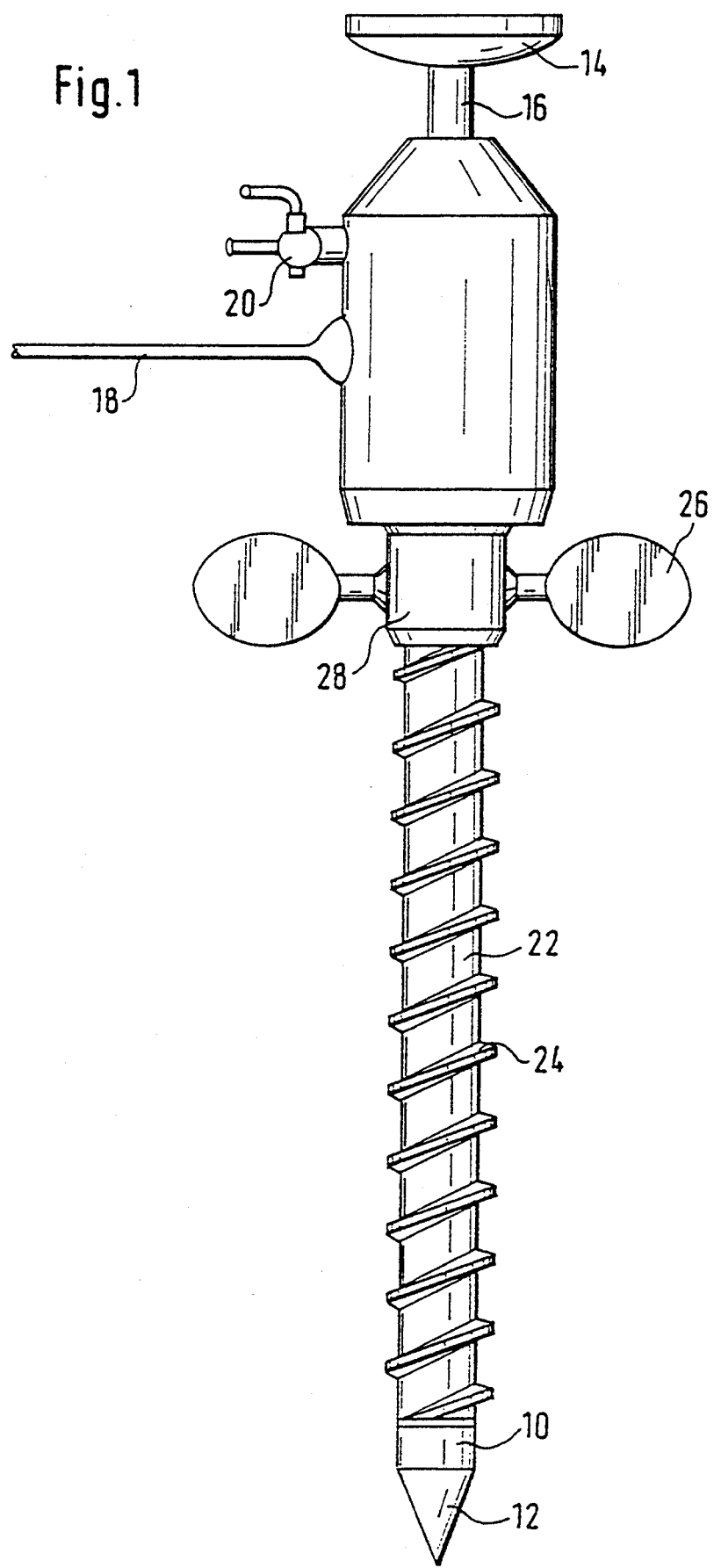

United States Patent [19]

Riek et al.

[11] Patent Number: 5,431,151
[45] Date of Patent: * Jul. 11, 1995

[54] INSTRUMENT FOR THE PENETRATION OF BODY TISSUE

[75] Inventors: Siegfried Riek, Rottweil; Karl-Heinz Bachmann; Thomas Gaiselmann, both of Villingendorf, all of Germany

[73] Assignee: Partomed Medizintechnik GmbH, Villingindorf, Germany

[*] Notice: The portion of the term of this patent subsequent to Dec. 21, 2010 has been disclaimed.

[21] Appl. No.: 168,213

[22] Filed: Dec. 17, 1993

Related U.S. Application Data

[63] Continuation of Ser. No. 779,730, Oct. 23, 1991, Pat. No. 5,271,380.

[30] Foreign Application Priority Data

Nov. 6, 1990 [DE] Germany ............... 40 35 146.7

[51] Int. Cl.⁶ ............................................. A61B 1/00
[52] U.S. Cl. ................................. 600/164; 604/164; 600/114; 600/156; 600/166; 600/182
[58] Field of Search ............. 128/4, 6, 7, 754, 207.29; 606/1, 46, 167, 170, 180, 185, 191; 604/164, 165, 166, 168, 900; 356/241

[56] References Cited

U.S. PATENT DOCUMENTS

| | | |
|---|---|---|
| 207,932 | 9/1878 | Alvord . |
| 3,224,320 | 12/1965 | Knudsen . |
| 3,357,433 | 12/1967 | Fourestier et al. ............. 356/241 |
| 3,437,747 | 4/1969 | Sheldon . |
| 3,556,085 | 1/1971 | Takahashi . |
| 3,870,036 | 3/1975 | Fiore . |
| 3,961,621 | 6/1976 | Northeved ................. 128/6 X |
| 4,191,191 | 3/1980 | Auburn ................. 606/185 X |
| 4,222,375 | 9/1980 | Martinez . |
| 4,248,214 | 2/1981 | Hannah et al. . |
| 4,254,762 | 3/1981 | Yoon . |
| 4,269,192 | 5/1981 | Matsuo . |
| 4,271,380 | 12/1981 | Riek et al. ................. 128/4 |
| 4,311,138 | 1/1982 | Sugarman . |
| 4,319,563 | 3/1982 | Kubota . |
| 4,356,826 | 11/1982 | Kubota . |
| 4,535,773 | 8/1985 | Yoon . |
| 4,537,593 | 8/1985 | Alchas . |
| 4,567,882 | 2/1986 | Heller . |
| 5,066,288 | 11/1991 | Deniega et al. . |
| 5,147,376 | 9/1992 | Pianetti . |
| 5,159,920 | 11/1992 | Condon et al. . |
| 5,250,068 | 10/1993 | Ideguchi et al. ............. 606/185 X |
| 5,256,149 | 10/1993 | Banik et al. ............. 604/164 |
| 5,290,276 | 3/1994 | Sewell, Jr. ............. 606/15 |

FOREIGN PATENT DOCUMENTS

| | | |
|---|---|---|
| 0312787 | 9/1988 | European Pat. Off. . |
| 0369936 | 11/1989 | European Pat. Off. . |
| 0369937 | 11/1989 | European Pat. Off. . |
| 0347140 | 12/1989 | European Pat. Off. . |
| 1370580 | 7/1964 | France . |
| 2218901 | 10/1973 | Germany . |
| 2538758 | 3/1977 | Germany . |
| 4020956 | 1/1991 | Germany ............. 606/185 |
| 4133073 | 4/1992 | Germany . |
| 4116648 | 12/1993 | Germany . |
| 942730 | 7/1982 | U.S.S.R. . |
| 1328658 | 3/1987 | U.S.S.R. . |

*Primary Examiner*—Stephen R. Crow
*Assistant Examiner*—Beverly A. Meindl
*Attorney, Agent, or Firm*—Irvin A. Lavine

[57] ABSTRACT

An instrument is described for the penetration of body tissue with a hollow shaft, the point of which is formed as a conical, beveled, or tapered window. An optic with a lighting unit is brought into the point through the hollow shaft. The optic ends at an axial distance behind the summit of the point. The instrument can be inserted within view. In so doing, the entry of the point can observed over the entire surface area thereof. Preferably, a second optic is run to the summit of the point, which in addition enables improved observation of the area lying directly in front of the point.

70 Claims, 6 Drawing Sheets

INSTRUMENT FOR THE PENETRATION OF BODY TISSUE

This application is a continuation of U.S. patent application Ser. No. 07/779,730, filed Oct. 23, 1991, now U.S. Pat. No. 5,271,380.

The invention relates to an instrument for the penetration of body tissue, with a hollow shaft, ending in a point formed as a conical window, and with optics and lighting units.

Instruments of this type serve particularly as trocars to create an artificial access to body cavities or organs, which do not possess any natural communicating passage with the exterior. The instrument has a point, which serves to pierce the body tissue and to widen the perforation opening to the diameter of the shaft. During use as a trocar, a sleeve Surrounding the shaft is pushed together with the trocar into the perforation opening and, after removal of the trocar, represents an artificial access to the body cavity, the said access through which endoscopes, instruments, and the like can be introduced into the interior of the body.

The insertion of the trocar, even with the advantageous selection of an injection site, entails the risk of damaging blood vessels in subcutaneous fatty tissue, in fascia, and in the peritoneum ("abdominal membrane"), thus vessels in the abdominal wall. There is the further risk after penetration of the abdominal wall that the vessels in the abdominal area (abdominal cavity) and organs in the abdominal area, such as the large intestine, small intestine, omentum majus (greater omentum), and retroperitoneally located vessels and structures can be damaged. Especially at risk for damage are the small intestine and the omentum majus, if adhesions and concretions with the anterior abdominal wall are present, so that during penetration of the abdominal wall, structures adhering to the said wall may be pierced at the same time before the trocar enters the free abdominal cavity. To reduce the risk of damage, particularly to the intestine and omentum majus, a hollow needle can be passed through the abdominal wall first while the abdominal wall is lifted, to introduce gas into the abdominal cavity and to distance the abdominal wall from the underlying omentum majus and intestine for the subsequent insertion of the trocar. In that case as well, however, there is a residual risk of damage during the insertion of the hollow needle and the trocar.

An instrument disclosed in DE [West German Patent] 29 22 239 C2 has an outer tube, which is beveled at the anterior distal end thereof, to form an insertion point. Two fiber-optic light bundles are run in the outer tube to the point, with the anterior end faces of the said bundles lying in the plane of the beveled face of the outer tube. The light from a light source is directed through a fiber-optic light bundle and emerges at the distal point. The second fiber-optic light bundle receives the reflected portion of this emerging light and directs the said portion to an optically sensitive element. The measured intensity of the reflected light provides information about the anatomic structure in front of the point. The alteration in the intensity of reflected light shows when the point of the instrument approaches an organ in the free abdominal cavity. During the penetration of successive tissue layers in the abdominal wall or when the point enters adhesions and concretions of organs connected to the abdominal wall, however, the reflectivity of the tissue structures in front of the point remain essentially unchanged, so that the entry of the point cannot be controlled. The beveling of the outer tube produces an insertion point, which is located near the shell of the outer tube laterally beside the emerging plane of the fiber-optic light bundles and projects beyond the said plane. The insertion point thereby limits the field of vision that can be controlled via the optic system.

A fiber-optic system functioning as a microscope is disclosed in DE-AS [Examined West German Patent Application] 16 16 107, the said system which is placed in an insertion needle. The outer tube surrounding the optic system in the needle is beveled at the distal end to form the insertion point. The tissue in front of the needle tip can be observed microscopically via the optic system. The needle cannot be employed as a trocar, because the smaller diameter thereof does not cause the widening of the perforation opening. The insertion point produced by the beveling of the outer tube produces a blind area which restricts the field of vision.

Endoscopes have been disclosed in EP [European Patent] 0 369 937 A1, EP 0 369 936 A1, and EP 0 347 140 A1, the said endoscopes which possess an outer tube wherein the fiber-optic systems are run to the point. The said endoscopes enable observation in the direction of fiber-optic fibers emerging at the point. The endoscopes are not suitable for the penetration of tissue.

A massive trocar is disclosed in DE-OS [Unexamined West German Patent Application] 22 18 901, the trocar sleeve of which possesses an outer screw thread at the proximal end thereof. The screw thread has the purpose of fixing the placed trocar sleeve more reliably against an axial displacement in the trocar-produced perforation opening.

The invention has as its object the provision of an instrument for the penetration of body tissue, the said instrument which reduces as much as possible the risk of damage to vessels, organs, and the like via improved optic control during insertion.

The above object is achieved with an instrument according to the type described in the invention by means of a hollow shaft with a pointed conical end of transparent material, with optics and lighting such that the entire pointed, transparent end is capable of being illuminated and observed.

Advantageous embodiments of the invention described herein are also claimed.

The novel instrument has a hollow shaft. The point or at least the distal end portion of the point is made as a window from a suitable transparent material, e.g., from glass, quartz glass, Plexiglas, or the like. An optic is run through the hollow shaft to the point, e.g., an optic with glass fiber-optic light guide, as is used in endoscopes. Furthermore, a lighting unit is run in the hollow shaft to the point. The lighting unit can be integrated into the optic in that fiber-optic fibers employed for producing illumination are placed in the tract of the optic. Likewise it is possible to run the illumination separately from the optic through the shaft to the point or also to combine lighting units integrated in the optic with additional separately introduced lighting units. The optic ends at an axial distance behind the summit of the point, so that the entire surface area of the conical window cab be illuminated by the optic and observed. The operator thus has a view during the advance of the instrument of the structures to be penetrated and lying in front of the instrument point. The operator can thus recognize blood vessels, for example, before these are struck by the point of the instrument, and avoid the said vessels. In particular, the important step of the penetration of the peritoneum can proceed within view. The semi-transparent peritoneum almost permits a look into the abdominal cavity before total penetration, so that the underlying omentum majus, intestines, and vascular structures in the peritoneum are discernable and damage thereto can be avoided. In addition, during the advance of the instrument the operator can observe structures penetrated by the point and passing laterally by the surface area of the window, and thus obtains a feeling for the penetration of the point and for the rate of advance.

Because of its conical, beveled, or tapered form, the window is useful as a point, which effects both the penetration of the tissue and also the widening of the perforation opening. The special shape of the conical, beveled, or tapered window is thereby of lesser significance. Preferred is a right circular cone, because the said cone is the most simple to fabricate and produces the lowest optic distortion during observation. However, other conical, beveled, or tapered forms are also essentially possible, e.g., with a polygonal base and with a slightly crowned or slightly recessed surface line.

Because the lighting unit is placed within the point-forming window and illumination occurs through this window, it can be advantageous to dereflect the inner surface of the window. The conical, beveled, or tapered form of the window in a hollow point, however, of necessity causes an inclination of the inner window surfaces relative to the optical axis of the illumination and the optic, so that interfering reflections are minor in any event.

In an advantageous embodiment, the observation of the area lying in front of the point of the instrument can be improved still further, so that a combination of the static picture of the area lying in front of the point of the instrument with the dynamic picture of the point's advance is created for the operator. In the said embodiment, in addition to the optic viewing the entire surface area of the window, a second optic, which is formed as a thin flexible glass fiber optic, is run to the window-forming point. The said second optic is run laterally past the first optic to the window-forming point and ends at the face of the window-forming point. The said second optic with the smallest possible diameter thus provides the view of the area in front of the point, whereas the first optic enables the view of the penetrated structures adjacent to the surface area of the window. The small diameter of the second fiber optic essentially does not obstruct the observation through the first optic.

In this embodiment, the operator can observe both the advance of the instrument's point with the use of two oculars, to obtain a feeling for the path and rate of advance, and also observe the structures lying in front of the point, to avoid damage to vessels, organs, the intestine, or the omentum majus.

In all cases, the optics are formed preferably as a wide-angle optic (fish-eye optic), to offer the operator the largest possible field of vision and to enable observation through the entire surface area of the conical, beveled, or tapered window.

If the instrument is fashioned as a trocar-sleeve, then upon the insertion of the trocar within view the possibility of avoiding structures at risk for damage can be employed optimally if the sleeve has an external thread. The sleeve is mounted axially stationary but rotatable on the trocar. By turning of the sleeve, the external thread thereof takes hold of the tissue and effects the advance of the trocar. The trocar with its optic does not turn in so doing. The advance via the sleeve provided with the thread enable a steady, smooth entry of the trocar point, without the operator needing to exert axial pressure on the trocar. This promotes delicate guidance of the trocar point in the area of structures at risk for damage.

To be able to turn the sleeve without great effort, the said sleeve can be actuated manually via a ratchet. Actuation via an electric motor with appropriate gear reduction is equally possible.

The novel instrument is preferably employed as a trocar for the penetration of the abdominal wall and for the introduction of a trocar-sleeve into the perforation opening. Furthermore, the novel instrument can be used as a perforation needle with a thin shaft to penetrate the abdominal wall and to introduce gas into the abdominal area, so that the abdominal wall can be lifted off the internal organs before the insertion of the trocar. Finally, the novel instrument with a very fine shaft can be used in prenatal diagnosis, to pierce the amniotic sac for the removal of amniotic fluid, whereby the view through the point of the instrument safely precludes damage to the fetus.

Figure 2:
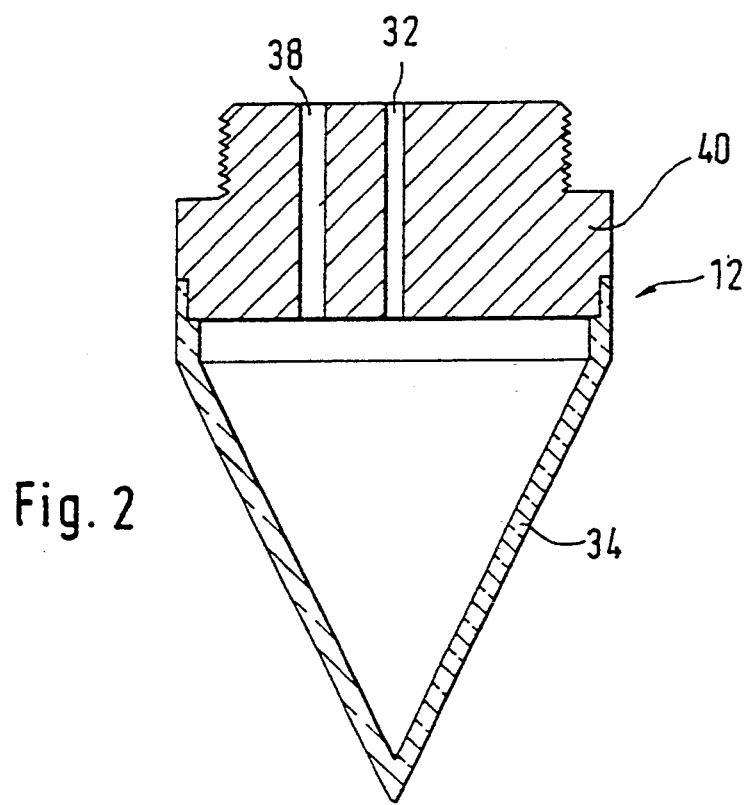
Figure 3:
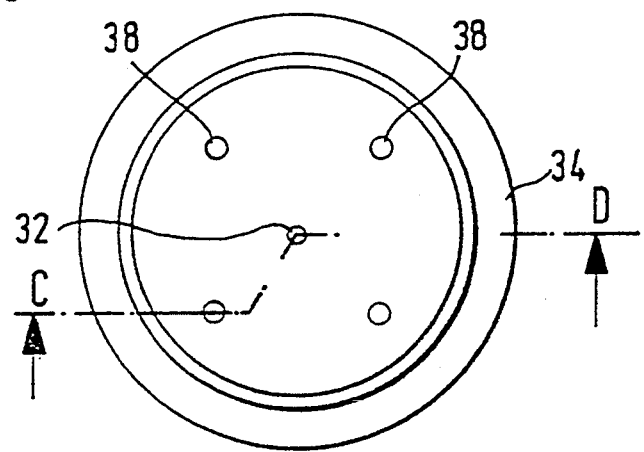
Figure 4:
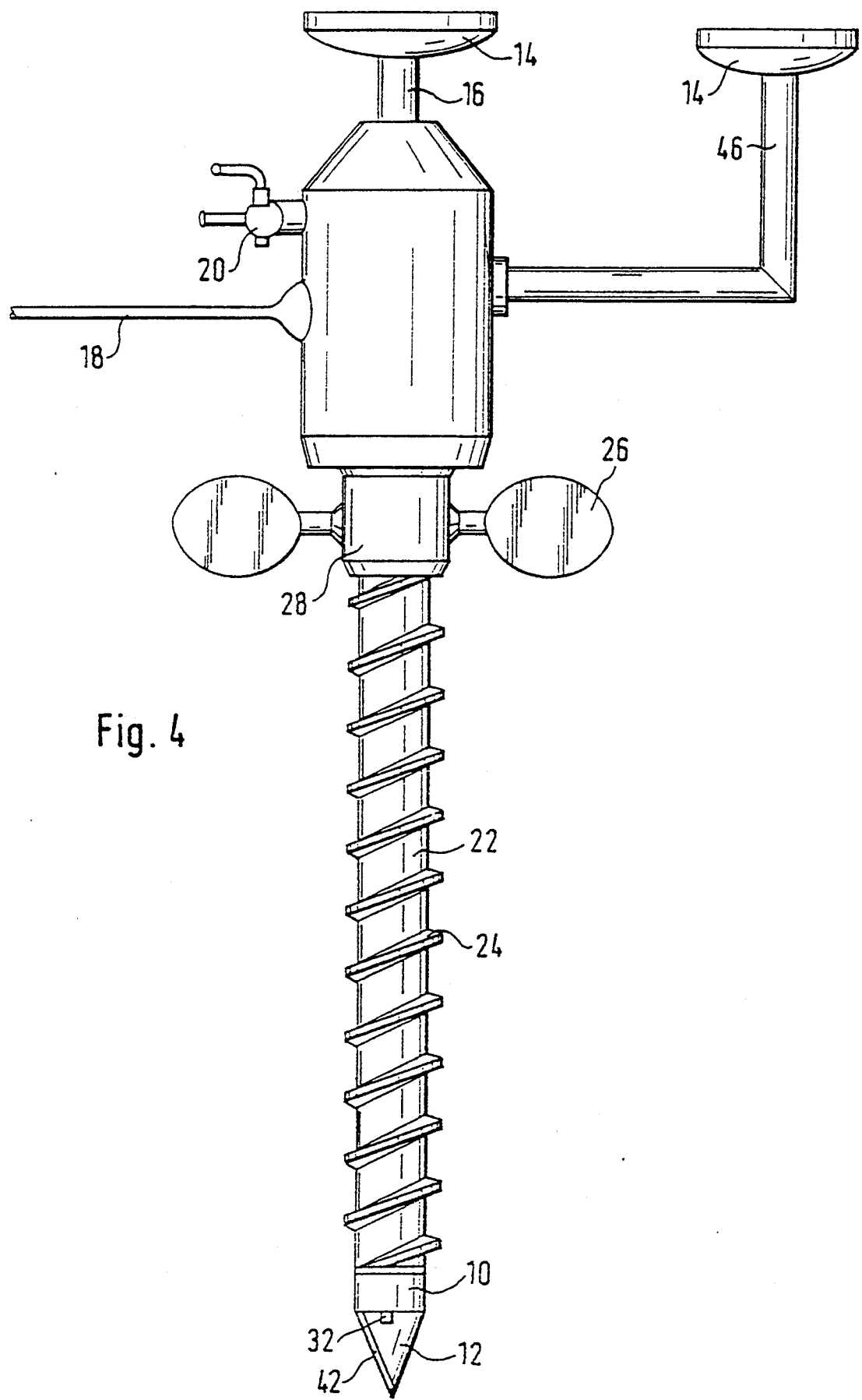
Figure 5:
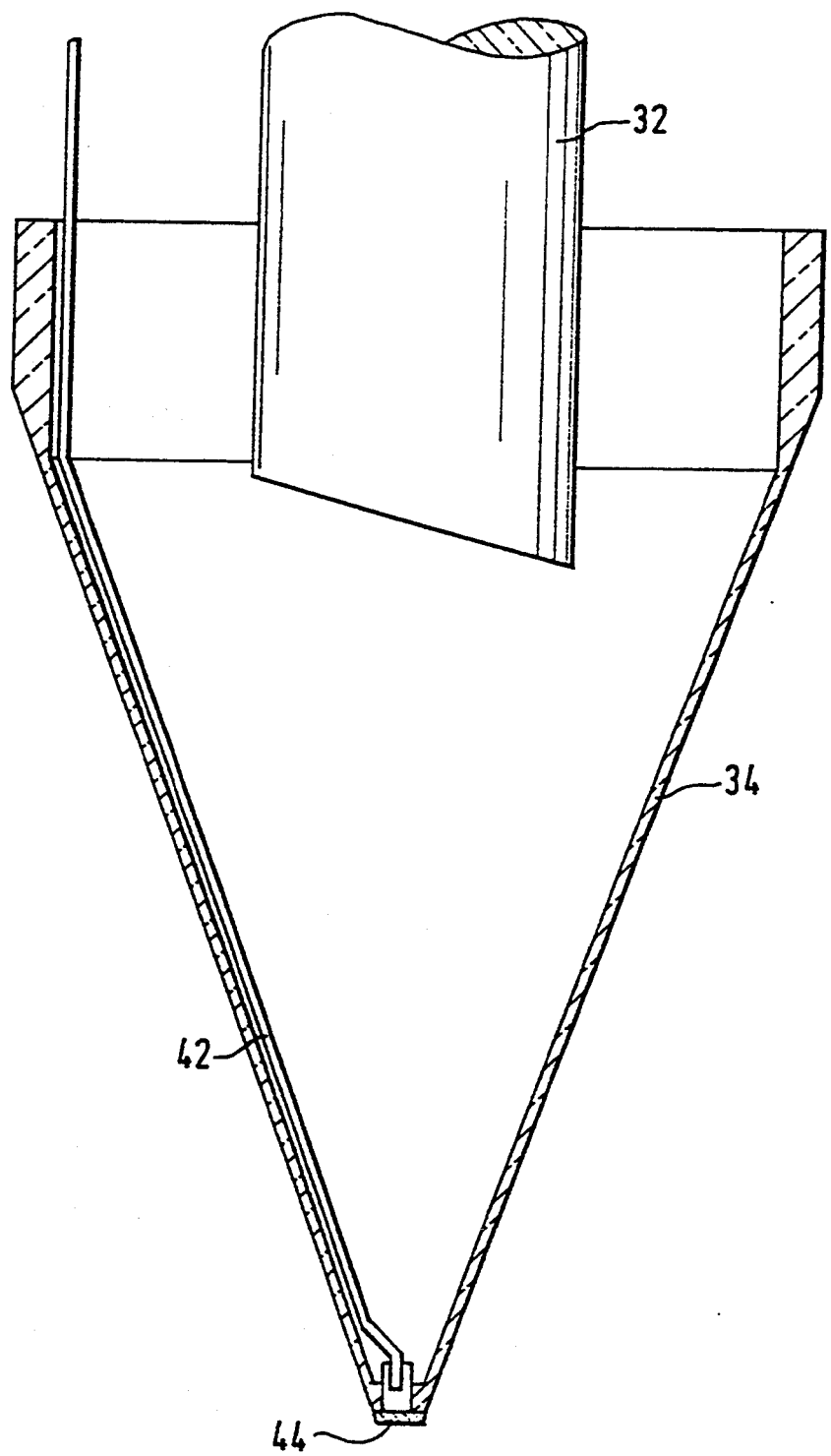
Figure 6:
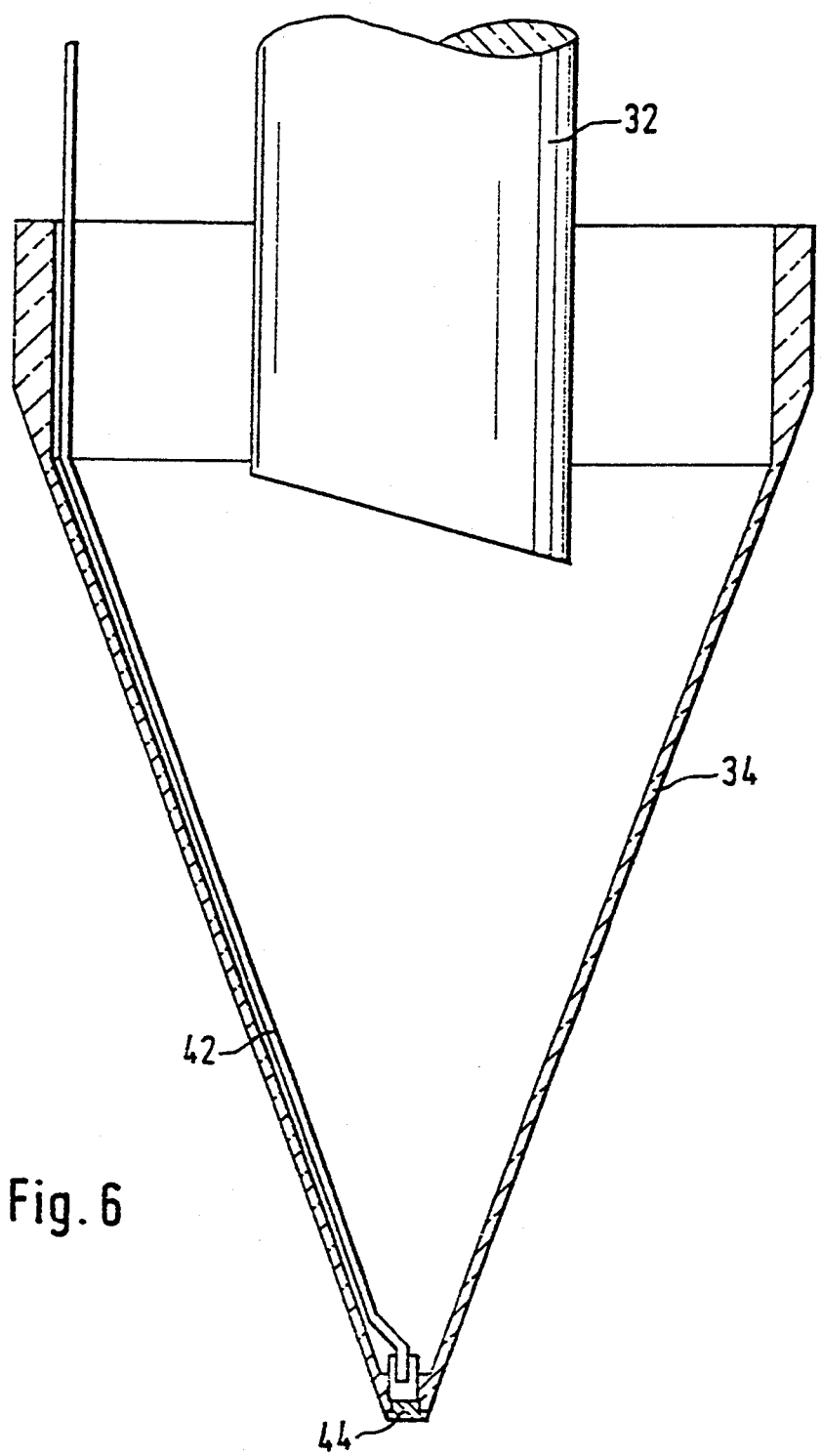

The invention will be described in greater detail below on the basis of embodiments presented in the figures. Shown are:

FIG. 1 a side view of an instrument fashioned as a trocar,

FIG. 2 an axial section of the point of the trocar,

FIG. 3 a front view of the point from the back,

FIG. 4 a side view of the trocar in another embodiment,

FIG. 5 an axial section of the point of the trocar in FIG. 4,

FIG. 6 an axial section, corresponding to FIG. 5, of a modified embodiment, and

Figure 7:
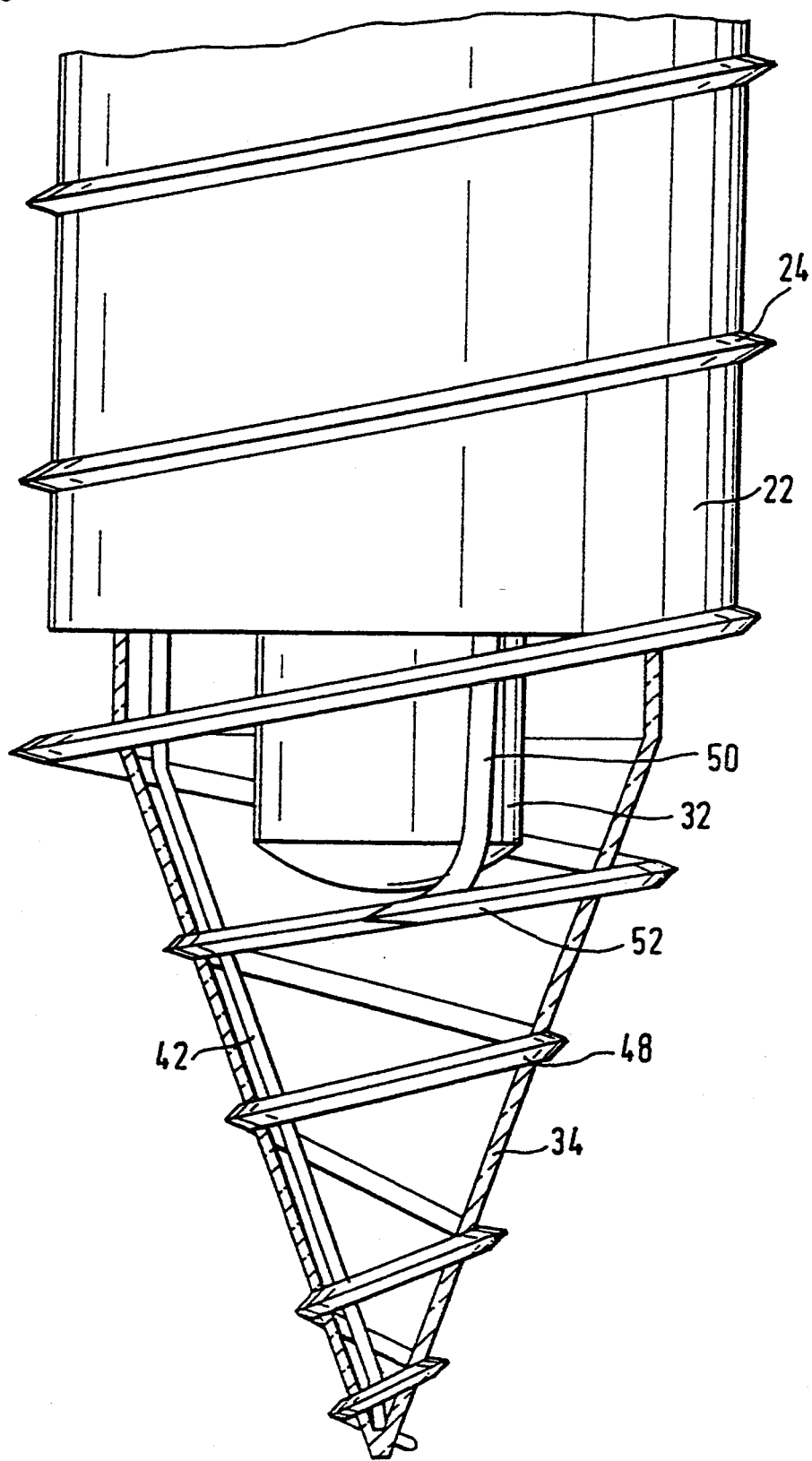

FIG. 7 a side view of the point of the trocar in an additional embodiment.

The trocar shown in FIG. 1 has a hollow cylindrical shaft 10 made of steel, with a point 12, described below, inserted in the distal anterior end thereof. The eyepiece 16, provided with a cup 14, of an optic 16, placed coaxially in shaft 10 and described below, is placed at the proximal posterior end of the shaft 10. Furthermore, a fiber-optic light guide 18 of a lighting unit, described below, is introduced laterally into the posterior end of shaft 10. Finally, at the posterior end of shaft 10 an insufflation cock 20 is placed, through which for example, $CO_2$ gas can be delivered in a manner known per se to outlets, not depicted, at the anterior distal end of the shaft.

A sleeve 22 is mounted on the shaft 10 axially stationary but rotatable. The sleeve 22 has a stub thread 24 on its outer surface. The sleeve 22 can be actuated to rotate relative to shaft 10 via a ratchet 28 having a toggle handle 26. An electric motor drive for the sleeve 22 is also possible. If sleeve 22 is turned on the inserted trocar, the thread 24 effects an axial advance of the trocar, whereby the said trocar itself does not turn. With the aid of the sleeve 22 provided with the thread 24, the trocar can be advanced slowly and delicately into the tissue by the operator without the exertion of axial pressure.

As is evident from FIGS. 2 and 3, a point 12 is mounted, e.g., screwed in or soldered in, in the distal end of hollow shaft 10, and the proximal end of point 12 has approximately the same size and shape as the distal end of hollow shaft 10. The base of the point has a peripheral boundary and the surface of the point is at a plurality of straight lines each extending from the apex to the peripheral boundary of the point 12.

The optic 32 is inserted into an axially central drill hole leading to point 12. The optic 32 is run axially through the entire shaft 10 and ends at the proximal posterior end in eyepiece 16. The distal anterior end of optic 32 is cemented or glued in place into the drill hole of point 12.

Optic 32 is a fish-eye optic known per se, as is employed, for example, in endoscopes. A fiber-optic light guide optic is used preferentially.

Four additional drill holes, arranged equidistant around the central drill hole, are provided in point 12 parallel to the central drill hole incorporating the optic 32. A lighting unit 38 in the form of a fiber-optic light guide is inserted into the said drill holes in each case. The fiber-optic light guides of the lighting units 38 are run through the shaft 10. Light is supplied to the lighting units 38 via the fiber-optic light guide 18 and a branching.

The point 12 comprises an end flange 40 made of steel, which is mounted into the distal end of hollow shaft 10. An optic window 34 in the form of a hollow imperforate cone, bevel, or taper, made of glass, quartz glass, Plexiglas, or diamond is placed in front of end flange 40 and attached by gluing or cementing.

The end flange 40 has the central, axially passing drill hole, into which the optic 32 is inserted. Furthermore, the four drill holes, arranged around the optic, for the lighting units 38 are provided in the end flange 40. The optic 32 and lighting units 38 end at the anterior face of the end flange 40. The lighting units 38 thus illuminate the entire cone, bevel, or taper of the window 34 and optic 32 enables observation of the tissue penetrated by point 12 through the entire 360° cone surface of window 34. The interior surface of window 34 can be dereflected if necessary.

In addition or instead of the said indirect illumination, direct illumination can also be effected, if a lighting unit, e.g., in the form of a light-conducting optic fiber, is integrated into the optic 32, the said fiber to which light is also supplied via the fiber-optic light guide 18.

The window 34 can form a sharp point having an apex in advance of hollow shaft 10, which enables easy penetration of tissue with the trocar. Because the optic 32 does not emerge on the face of the point 12 but rather in the face, forming the base of the point 12, of the end flange 40, an optic 32 with a larger diameter can also be used, e.g., a typical rod lens system (so-called Hopkins optic), which has an improved light efficiency. Here as well, the lighting unit 38 can be integrated into the optic 32. The optic 32 in this case as well is naturally a fish-eye optic.

Another embodiment is shown in FIGS. 4, 5, and 6.

In the said embodiment, the optic window 34 is formed as a transparent hollow cone, bevel, or taper placed on an end flange 40 of the point 12, as is described with regard to FIGS. 2 and 3. The first optic 32 is mounted axially in the center, the said optic which permits observation of the entire cone, bevel, or taper surface area of the window 34 preferably as a rod lens system.

In addition to the said first optic 32, a second optic 42 is run through the shaft 10 to the point 12. The second optic 42 is run eccentrically to the first optic 32 through the end flange 40 and proceeds interiorly along the hollow-cone window 34 to the apex of point 12. The second optic 42 emerges through the face of the conical, beveled, or tapered window 34 at the apex of the point 12. In so doing, the face can be formed by the distally most anterior part of the second optic 42. To protect the second optic 42 from pressure and soiling, a window 44 can be provided in the face in front of the second optic 42. The said window 44 can be prepared as a ground surface from the material of the window 34, as is shown in FIG. 5, or can be inserted into window 34, and for example, supported axially by a collar, as is shown in FIG. 6. The second optic 42 preferably contains an integrated lighting unit. The second optic is preferably fashioned as a thin fiber-optic light guide optic with a diameter of 0.2 to 0.8 mm. Preferably, the second optic 42 is flexible, so that it can be run interiorly along window 34. The proximal posterior end of the second optic 42 is brought out laterally from shaft 10 and equipped with a second ocular 46, so that the operator can observe binocularly via both optics 32 and 42.

The second optic 42, run in the conical, beveled, or tapered window 34 to the apex of the point 12, virtually does not obstruct the view of the first optic 32, because the second optic 42 has a small diameter and preferably consists of transparent glass fibers.

The embodiment in FIGS. 4 to 6 gives the operator optimal information upon insertion of the trocar. Via the first optic 32 and the conical, beveled, or tapered window 34, he can observe the tissue structures, which have been passed through at the time, during penetration of the tissue to obtain the necessary information on the position of the point and the rate of advance. Via the second optic 42, he has a view of the tissue structures lying ahead of the point 12 immediately before the penetration thereof. The penetration of the peritoneum in particular can proceed within view, whereby the still intact semitransparent peritoneum directly before the point 12 permits a look into the abdominal cavity via the second optic so that damage to vessels in the peritoneum and the underlying omentum majus and intestines can be avoided during the penetration of the peritoneum.

In another embodiment shown in FIG. 7, a gripping element is mounted at the point of the trocar, the said gripping element which has the purpose of firmly holding the body tissue during penetration against the pressure of the trocar point. The body tissue, e.g., peritoneum, cannot thereby avoid the trocar point and cannot be vaulted inwardly into the abdominal cavity.

As FIG. 7 shows, the gripping element consists of a rotatable spiral 48, mounted externally to the conical, beveled, or tapered window 34, the said spiral which, for example, is made from a wire having surfaces converging to a line and is fitted to the conical, beveled, form of the window 34. The spiral 48 extends to adjacent to the distal end of window 34, and is bent at its posterior end into an axis-parallel connecting piece 50, which is shaped at its end into a ring, which is not visible in the figure and is mounted rotatably in a circumferential groove of the shaft 10 of the trocar. By means of the said ring, the spiral screw 48 is thus mounted rotatably on the conical window 34 and firmly held axially. The thread 24 of the sleeve 22 is brought out through the anterior distal sleeve end and acts as a driver point 52 upon the posterior end of the spiral 48, to carry it along during the rotation of the sleeve 22.

To penetrate the body tissue, e.g., the patient's abdominal wall, the sleeve 22 is caused to rotate, whereby it causes the spiral 48 on the conical, beveled, or tapered window 34 to rotate via the driver point 52. Via the rotating spiral 48 and the attached thereto thread 24, the trocar bores into the tissue like a corkscrew, advancing and penetrating without the said tissue being able to evade the trocar point. As soon as the tissue is penetrated and the trocar point is, for example, in the abdominal cavity, the trocar together with the spiral 48 held axially on its point can be withdrawn from the sleeve 22. The sleeve 22 can then be used for the insertion of surgical instruments or the like.

We claim:

1. An instrument for the direct penetration of body tissue comprising:
    a rigid elongated shaft having an axis, an exterior surface, and a distal end,
    a sharp pointed, tapering window at the distal end of said shaft having an apex in advance of said shaft, said apex being within an axial projection of the exterior surface of said shaft, and
    said window having a base at the distal end of said shaft, said base having a peripheral boundary, said sharp pointed, tapering window having an external surface at or within a straight line extending from said apex to the boundary of said base,
    whereby light may be transmitted through said window and said instrument may readily penetrate body tissue.

2. An instrument according to claim 1, wherein said shaft is a hollow shaft.

3. An instrument according to claim 2, wherein said window is a right circular cone.

4. An instrument according to claim 1, said base of said window being of substantially the same lateral size and shape as the distal end of said shaft.

5. An instrument according to claim 1, wherein said instrument has a sleeve surrounding said shaft so as to provide a portal into a body cavity when said instrument is removed from a body cavity.

6. An instrument according to claim 5, wherein said instrument has an insufflation cock placed at the proximal end of said shaft for delivering or removing a gas into or from said body cavity.

7. An instrument according to claim 6, wherein said instrument is a trocar.

8. An instrument according to claim 1 or 6, further comprising:
    an optical element within said shaft having a distal end formed as a lens spaced from said apex of said window and positioned to receive the image of at least a part of a body adjoining or in close proximity to the exterior of said window, and
    a light conductor within said shaft for conducting light from a light source and directing light to said window.

9. An instrument according to claim 8, wherein said lens is a wide angle lens.

10. An instrument according to claim 9, wherein at least one of said optical element and said light conductor comprises a fiber-optic.

11. An instrument according to claim 10, wherein at least one of said optical element and said light conductor is supplied by a structure including a source of light and a lens for viewing.

12. An instrument for the direct penetration of body tissue comprising:
    an elongated rigid shaft having a distal end,
    a transparent window with a sharply tapering generally conical configuration at and substantially covering the distal end of said shaft, and having a distal end in advance of said shaft, and
    means outwardly of said window and extending to adjacent to said distal end for effecting the advance of said instrument into body tissue to create or expand an artificial access to a body cavity.

13. An instrument according to claim 12, wherein said rigid shaft is hollow.

14. An instrument according to claim 13, wherein said window is configured as a right circular cone.

15. An instrument according to claim 14, wherein said right circular cone has a sharp point.

16. An instrument according to claim 14, wherein said instrument has a sleeve surrounding said shaft, so as to provide a portal into a body cavity when said instrument is removed from a body cavity.

17. An instrument according to claim 16, wherein said instrument has an insufflation cock placed at the proximal end of said shaft for delivering or removing a gas into or from a body cavity.

18. An instrument according to claim 17, wherein said instrument is a trocar.

19. An instrument according to claim 12 or 18, further comprising:
    an optical element within said shaft having a distal end formed as a lens spaced from said apex of said window and positioned to receive the image of at least a part of a body adjoining or in close proximity to the exterior of said window, and
    a light conductor within said shaft for conducting light from a light source and directing light to said window.

20. An instrument according to claim 19, wherein said lens is a wide angle lens.

21. An instrument according to claim 20, wherein at least one of said optical element and said light conductor comprises a fiber-optic.

22. An instrument according to claim 21, wherein at least one of said optical element and said light conductor is supplied by a structure including a source of light and a lens for viewing.

23. The instrument of claim 12, said means for effecting the advance of said instrument comprising a penetrating element having first and second surfaces converging substantially to a line lying outwardly of said transparent window.

24. The instrument of claim 23, wherein said penetrating element is substantially helical.

25. An instrument for the direct penetration of body tissue comprising:
    an elongated shaft having a distal end,
    a transparent window at the distal end of said shaft having a generally conical configuration and having a distal end in advance of said shaft, and
    penetration means outwardly of said transparent window extending to adjacent to the distal end thereof for piercing said body tissue to create or expand an artificial access to a body cavity.

26. An instrument according to claim 25, wherein said shaft is a rigid hollow shaft.

27. An instrument according to claim 26, wherein said window is configured as a right circular cone.

28. An instrument according to claim 27, wherein said right circular cone has a sharp point.

29. An instrument according to claim 25, wherein said instrument has a sleeve surrounding said shaft so as to provide a portal into said body cavity when said instrument is removed from said body cavity.

30. An instrument according to claim 29, wherein said instrument has an insufflation cock placed at the proximal end of said shaft for delivering or removing a gas into or from said body cavity.

31. An instrument according to claim 30, wherein said instrument is a trocar.

32. An instrument according to claim 25 or 31, further comprising:
  an optical element within said shaft having a distal end formed as a lens spaced from said apex of said window and positioned to receive the image of at least a part of a body adjoining or in close proximity to the exterior of said window, and
  a light conductor within said shaft for conducting light from a light source and directing light to said window.

33. An instrument according to claim 32, wherein said lens is a wide angle lens.

34. An instrument according to claim 33, wherein at least one of said optical element and said light conductor comprises a fiber-optic.

35. An instrument according to claim 34, wherein at least one of said optical element and said light conductor is supplied by a structure including a source of light and a lens for viewing.

36. The instrument of claim 25, wherein said penetration means for effecting the advance of said instrument comprising a penetrating element having first and second surfaces converging substantially to a line lying outwardly of said transparent window.

37. The instrument of claim 36, wherein said penetrating element is substantially helical.

38. An instrument for the direct penetration of body tissue comprising:
  a rigid elongated shaft having a distal end,
  a sharp, generally conical point at the distal end of said shaft having a base at the distal end of said shaft and an apex in advance of said shaft, said base having a peripheral boundary,
  at least the distal end portion of said sharp, generally conical point being transparent, said sharp, generally conical point being at or within any straight line extending from said apex to the boundary of the base to thereby facilitate penetration of body tissue,
  whereby body tissue may be viewed through said transparent distal end portion of said window as said shaft causes said sharp, generally conical point to penetrate body tissue.

39. The instrument according to claim 38, wherein said point is transparent.

40. The instrument according to claim 38, wherein said shaft is a hollow shaft.

41. The instrument according to claim 40, wherein said generally conical point is a right circular cone.

42. An instrument according to claim 41, wherein said instrument has a sleeve surrounding said shaft so as to provide a portal into said body cavity when said instrument is removed from said body cavity.

43. An instrument according to claim 42, wherein said instrument has an insufflation cock placed at the proximal end of said shaft for delivering or removing a gas into or from said body cavity.

44. An instrument according to claim 38 or 43, further comprising:
  an optical element within said shaft having a distal end formed as a lens spaced from said apex of said window and positioned to receive the image of at least a part of a body adjoining or in close proximity to the exterior of said window, and
  a light conductor within said shaft for conducting light from a light source and directing light to said window.

45. An instrument according to claim 44, wherein at least one of said optical element and said light conductor comprises a fiber-optic.

46. An instrument according to claim 45, wherein at least one of said optical element and said light conductor is supplied by an endoscope.

47. The instrument according to claim 38, said point substantially covering the distal end of said shaft.

48. The instrument of claim 38, wherein said point has a surface which is without an opening or openings of sufficient size to permit flow of a substantial amount of fluid therethrough.

49. An instrument for penetration of body tissue comprising:
  a point element having a proximal end and a distal end, said point element being shaped to penetrate body tissue to create an opening therein and to enlarge the opening as the point element is advanced with the said distal end forward of said proximal end, said point element having a surface that converges to at least one real or virtual point,
  at least the distal end portion of said point element being transparent, and
  a rigid linear element having a distal end at the proximal end of said point element for advancing said point element into and withdrawing said point element from body tissue,
  whereby means for lighting and viewing may be positioned to illuminate body tissue and view body tissue exteriorly of said point element.

50. The instrument of claim 49, said proximal end of said point element being substantially coextensive with said distal end of said linear element.

51. The instrument of claim 49 or claim 50, wherein said point element is transparent.

52. The instrument of claim 49, said point element being truncated.

53. An instrument for the direct penetration and viewing of body tissue comprising:
  a rigid shaft having distal and proximal ends,
  a point element at the distal end of said shaft shaped to penetrate body tissue to enlarge an opening therein as the point element is advanced, said point element having a distal end, and at least part of said point element being transparent to permit viewing of body tissue therethrough, and
  an advancing element at said point element to facilitate the advance of said point element, said advancing element having first and second surfaces converging substantially to a line, said line lying outwardly of and adjacent to the distal end of said point element.

54. The instrument of claim 53, said point element being of greater transverse dimension adjacent said distal end of said rigid shaft and of lesser transverse dimension at parts thereof more remote from said distal end of said rigid shaft, said line extending from outwardly of a part of said point element having a greater transverse dimension to outwardly of a part of said point element having a lesser transverse dimension.

55. The instrument of claim 54, said last mentioned element being of spiral configuration.

56. The instrument of claim 53, wherein said transparent part of said point element positioned at the distal end thereof.

57. The instrument of claim 53, said point element being truncated.

58. The instrument of claim 53, wherein the transparent part of said point element extends through substantially 360°.

59. An instrument for penetration of body tissue comprising:
- an elongated shaft having a longitudinal axis and a distal end,
- a window at the distal end of said shaft, said window having a longitudinal axis and a distal end portion remote from said distal end of said shaft, at least the distal end portion of said window being transparent,
- said window having a surface configuration substantially symmetrical about the longitudinal axis thereof,
- said longitudinal axis of said window being in alignment with the longitudinal axis of said shaft, and
- at least one element outwardly of said window extending to adjacent to the distal end thereof and having first and second surfaces converging substantially to a line lying outwardly of said window, whereby light may be transmitted through at least a portion of said window and said element will effect the advance of said instrument into body tissue.

60. The instrument of claim 59, said window having a proximal end at and adjacent the distal end of said shaft, said proximal end of said window being of substantially the same lateral size and shape as the distal end of said shaft.

61. The instrument of claim 59, wherein said elongated shaft is rigid.

62. The instrument of claim 59, wherein said window is substantially entirely transparent.

63. The instrument of claim 59, wherein said window is of generally tapering configuration from its proximal end to its distal end, and converging to at least one real or virtual point at or adjacent the distal end thereof.

64. The instrument of claim 59, wherein said window is conical.

65. The instrument of claim 64, wherein said conical window is in the form of a right circular cone.

66. The instrument of claim 59, said window having a greater lateral extent at the proximal end thereof than at the distal end thereof, and having at least one surface extending from the proximal end to the distal end thereof.

67. The instrument of claim 66, wherein said surface is a single, generally conical surface.

68. The instrument of any one of claims 1, 12, 25, or 59, wherein said window has a surface which is without an opening or openings of sufficient size to permit flow of a substantial amount of fluid therethrough.

69. The instrument of claim 59, wherein the transparent part of said point element extends through substantially 360°.

70. The instrument of claim 49 or 53, wherein said point element has a surface which is without an opening or openings of sufficient size to permit flow of a substantial amount of fluid therethrough.

* * * * *

UNITED STATES PATENT AND TRADEMARK OFFICE
CERTIFICATE OF CORRECTION

PATENT NO. : 5,431,151
DATED : July 11, 1995
INVENTOR(S) : Siegfried Riek et al

It is certified that error appears in the above-identified patent and that said Letters Patent is hereby corrected as shown below:

Title page, item [56], "References Cited":

Change  "4,271,380  12/1981  Riek et al  128/4" to

_ _ 5,271,380  12/1993  Riek et al  128/4--

Signed and Sealed this

Fifth Day of December, 1995

Attest:

BRUCE LEHMAN

Attesting Officer

Commissioner of Patents and Trademarks